United States Patent [19]

Horwitz

[11] Patent Number: 5,786,326
[45] Date of Patent: Jul. 28, 1998

[54] METHOD FOR THE TREATMENT OF ATHEROSCLEROSIS AND VASCULAR INJURY BY PREVENTION OF VASCULAR SMOOTH MUSCLE CELL PROLIFERATION

[76] Inventor: Lawrence D. Horwitz, 9853 E. Ida Ave., Englewood, Colo. 80111

[21] Appl. No.: 796,791

[22] Filed: Feb. 6, 1997

Related U.S. Application Data

[63] Continuation-in-part of Ser. No. 383,180, Feb. 3, 1995.
[51] Int. Cl.$^6$ .............................. A01N 43/46; A61K 31/55
[52] U.S. Cl. .............................. 514/11; 514/17; 514/18; 514/212
[58] Field of Search .............................. 514/11, 17, 18, 514/212

[56] References Cited

PUBLICATIONS

Araujo et al., "Iron Overload Augments the Development of Atherosclerotic Lesions in Rabbits," *Arteriosclerosis, Thrombosis, and Vascular Biology*, vol. 15, No. 8, pp. 1172–1180, Aug. 1995.
Austin et al., "Intimal Proliferation of Smooth Muscle Cells as an Explanation for Recurrent Coronary Artery Stenosis After Percutaneous Transluminal Coronary Angioplasty," *J Am Coll Cardiol*, vol. 6, No. 2, pp. 369–375, Aug. 1985.
Crowley et al., "Platelet–Induced Vascular Smooth Muscle Cell Proliferation Is Modulated by the Growth Amplification Factors Serotonin and Adenosine Diphosphate," *Circulation*, vol. 90, No. 4, pp. 1908–1918, Oct. 1994.
Crowley et al., "Multiple growth factors are released from mechanically injured vascular smooth muscle cells," Denver Veterans Affairs Medical Center and University of Denver, pp. H1641–H1647, (date?).
De Bruyn et al., "Effect of acute Hypertension in the coronary circulation: role of mechanical factors and oxygen radicals," *Journal of Hypertension*, vol. 12, No. 2, pp. 163–172, 1994.
Foegh et al. "Early inhibition of myointimal proliferation by angiopeptin after balloom catheter injurty in the rabbit," *Journal of Vascular Surgery*, vol. 19, No. 6, pp. 1084–1091, 1994.
Gutteridge et al., "Inhibition of the Iron–Catalysed Formation of Hydroxyl Radicals from Superoxide and of Lipid Peroxidation by Desferrioxamine," *Biochem. J.*, 184, 469–472, 1979.
Hagen et al., "Reduction of Venin Graft Intimal Hyperplasia by ex vivo Treatment with Desferrioxamine Manganese," *J. Vascules*, 29: 405–409, 1992.
Kluger, Jeffrey, "Can We Stay Young?" *Time*, 90–94, 96, 98, Nov. 25, 1996.

Lindner et al., "Inhibition of Smooth Muscle Cell Proliferation in Injured Rat Arteries," *J. Clin. Invest.*, vol. 90, 2044–2049, Nov. 1992.
Lloyd et al., "Evidence That Desferrioxamine Cannot Enter Cells By Passive Diffusion," *Biochemical Pharmacology*, vol. 41, No. 9, 1361–1363, 1991.
Lucas et al, "Effects of Iron–Depletion on Cell Cycle Progression in Normal Human T Lymphocytes: Selective Inhibition of the Appearance of the Cyclin A–Associated Component of the p33$^{cdk2}$ Kinase," *Blood*, vol. 86, No. 6, 2268–2280, Sep. 15, 1995.
Porreca et al, "Antiproliferative Effect of Desferrioxamine on Vascular Smooth Muscle Cells In Vitro and In Vivo," *Arteriosclerosis and Thrombosis*, vol. 14, No. 2, 299–304, Feb. 1994.
Ross, Russell, The Pathogenesis of Atherosclerosis–An Update, *The New England Journal of Medicine*, 488–500, Feb. 20, 1986.
Schwartz et al., "Effect of External Beam Irradiation on Neointimal Hyperplasia After Experimental Coronary Artery Injury," *JACC*, vol. 19, No. 5, 1106–1113, Apr. 1992.
Summers et al., "Studies in Desferrioxamine and Ferrioxamine Metabolism in Normal and Iron–Loaded Subjects," *British Journal of Haematology*, 42, 547–555, 1979.
Van Lenten et al., "Lipid–induced Changes in Intracellular Iron Homeostasis In Vitro and In Vivo," *J. Clin. Invest.*, vol. 95, 2104–2110, May 1995.
Wagenvoort et al., "Primary Pulmonary Hypertension," *Circulation*, vol. XLII, 1163–1184, Dec. 1970.
Wong et al., "Characterization of Exochelins of *Mycobacterium avium*: Evidence for Saturated and Unsaturated and for Acid and Ester Forms," *Journal of Bacteriology*, vol. 178, No. 21, 6394–6398, Nov. 1996.
Wohrley et al., "Hypoxia Selectively Induces Proliferation in a Specific Subpopulation of Smooth Muscle Cells in the Bovine Neonatal Pulmonary Arterial Media," *J. Clin. Invest.*, vol. 96, 273–281, Jul. 1995.

*Primary Examiner*—Frederick Krass
*Attorney, Agent, or Firm*—Michael J. Ram; Marvin H. Kleinberg; Marshall A. Lerner

[57] ABSTRACT

A method for the treatment of atherosclerosis and vascular injury using exochelins, and more particularly exochelins of Mycobacterium tuberculosis, to prevent vascular smooth muscle cell proliferation. Delivery of an effective amount of a desferri-Exochelins to a living organism such as an animal or a human by oral, intravenous or direct delivery to the site at which the effect is desired will protect blood vessels in a living organism from restenosis following angioplasty or vascular surgery and will prevent or slow the progression of atherosclerosis, systemic hypertension, radiation damage to the vasculature, stenosis or closure of bypass grafts to the coronary arteries or other blood vessels following a surgical procedure and various forms of pulmonary hypertension.

24 Claims, 10 Drawing Sheets fig. 1A
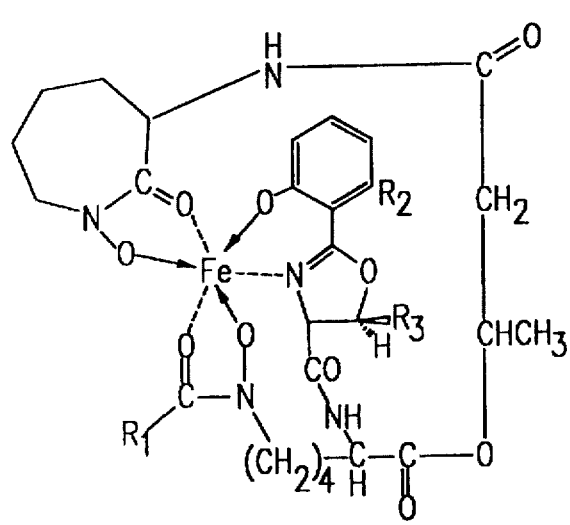
FERRIEXOCHELIN
fig. 1B
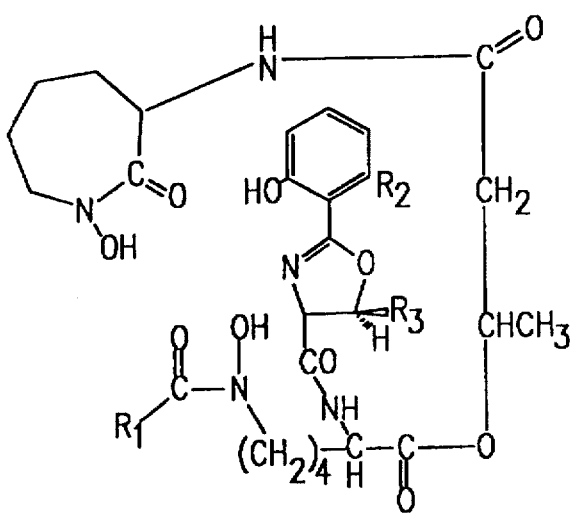
DESFERRIEXOCHELIN
fig. 1C
| $R_1$ | | $R_3$ | $M_r$ |
|---|---|---|---|
| $(CH_2)_N COOCH_3$ | $N=1-7$ | $H, CH_3$ | 716-828 |
| $(CH_2)_x CH=CH(CH_2)_y COOCH_3$ | $x+y=1-5$ | $H, CH_3$ | 742-826 |

ELUTION TIME (MINUTES)

(A) EXOCHELIN SATURATED SERINE SERIES

METHOD FOR THE TREATMENT OF ATHEROSCLEROSIS AND VASCULAR INJURY BY PREVENTION OF VASCULAR SMOOTH MUSCLE CELL PROLIFERATION

This application is a continuation-in-part of U.S. Ser. No. 08/383,180 filed Feb. 3, 1995. The present invention relates to a method for the treatment of atherosclerosis and vascular injury using exochelins, and more particularly the exochelins of Mycobacterium tuberculosis, to prevent vascular smooth muscle cell proliferation.

BACKGROUND

Inappropriate vascular smooth muscle proliferation is an integral component of the pathophysiology of several clinically important forms of vascular disease. Proliferation and migration of vascular smooth muscle cells are an important mechanism of the genesis of the atherosclerotic plaques that cause heart attacks, strokes or peripheral vascular disease (*N Eng J Med*;314:488–500, 1986). Restenosis after treatment of atherosclerotic vascular lesions with percutaneous transluminal angioplasty is a common adverse clinical outcome of this procedure. Restenosis involves a proliferative response of vascular smooth muscle at the site of the injury (*J Am Coll Cardiol*;6:369–375, 1985). Finally vascular smooth muscle proliferation has been proposed as an important component in the genesis of other forms of vascular injury or obstruction including closure of surgical bypass tracts (*J Vascular Research*;29:405–409, 1992), irradiation injury to the vasculature (*J Am Coll Cardiol*;19:1106–1113, 1992), systemic hypertension (*J Hypertension*;12:163–172, 1994) and neonatal or primary pulmonary hypertension (*J Clin Invest*;96:273–281, 1995 and *Circulation*;42:1163–1184, 1970).

In vitro cell culture preparations are often used to study vascular smooth muscle cell proliferation. Proliferation of cells in culture after exposure to serum containing growth factors or exposure to individual growth factors can be quantitated by measurement of radioactive thymidine uptake in the cells (*Circulation*;90:1908–1918, 1994). Compounds which inhibit growth of cultured vascular smooth muscle cells have the potential to prevent abnormal vascular smooth muscle proliferation in human diseases (*Am J Physiol*;269:H1641-H1647, 1995).

There is evidence that iron may be an important requirement for development of atherosclerosis. Iron overload due to injections of iron-dextran augments the formation of arterial atherosclerotic lesions in hypercholesterolemic rabbits (*Arterioscler Thromb Vasc Biol*;15:1172–1180, 1995). Oxidation of low density lipoprotein cholesterol is an important step in the early stages of development of atherosclerosis and is iron dependent (*J Clin Invest*;95:2104–2110, 1995). This may reflect the ability of free iron to catalyze the formation of highly reactive oxygen free radicals (*Biochem J*;184:469–472, 1979). However, chelation of iron inhibits cell growth or cell cycle progression in other models, including lymphocytes and neuroblastoma cell growth, where mechanisms unrelated to oxidation of low density lipoprotein cholesterol may occur (*Blood*;86:2268–2280, 1995). Finally the iron chelator deferoxamine prevents proliferation of vascular smooth muscle cells in vitro and prevents intimal thickening in vivo in rabbits (*Arterioscler Thromb*;14:299–304, 1994). Deferoxamine also reduces intimal smooth muscle proliferation in experimental vein grafts (*J Vascular Research*;29:405–409, 1992).

However, deferoxamine, a compound which is not extractable in chloroform and is therefore not soluble in lipid, has considerable limitations as a treatment for arteriosclerosis, restenosis or other forms of vascular injury. Deferoxamine has significant side effects when administered in high doses in vivo and generally achieves levels no higher than 10 μmol/L (*Br J Haematol*;42:547–555, 1979), which is not believed to be a high enough level to have an anti-proliferative effect in man. Deferoxamine can only be given intravenously, enters cells or tissues only very slowly by pinocytosis, and requires continuous administration because it is rapidly excreted (*Biochem Pharmacol*;41:1361–1363, 1991).

There is a need for preventing of atherosclerosis by providing an agent that is capable of iron chelation and prevention iron-mediated free radical production, but, in contrast to deferoxamine, is lipid-soluble. A lipid-soluble iron chelator with these properties is likely to be capable of oral or transcutaneous administration, and to have considerable efficacy in preventing both vascular smooth muscle cell proliferation and lipid oxidation, both major mechanisms in the development of atherosclerosis. Chronic administration of such a lipid-soluble iron chelator would be an ideal treatment to prevent or impede progression of atherosclerosis.

In addition, there is a need for prevention of restenosis after angioplasty, or other techniques that relieve vascular obstructions, by providing an agent that, like deferoxamine, is capable of iron chelation and preventing iron-mediated free radical production, but, is lipid-soluble. Accordingly, there is a need for prevention of atherosclerosis by providing an agent that is lipid-soluble, capable of preventing lipid peroxidation, and capable of oral administration.

Further, prevention of restenosis requires an agent which is effective within the first few hours after an angioplasty is performed (*J Clin Invest*;90:2044–2049, 1992);*J Vasc Surg* 1994; 19:1084–1091, 1992). Ideally this agent should be administered directly into the vessel which is being treated by angioplasty during the procedure or within a period of a few minutes or less thereafter. To be effective the agent must be rapidly taken up by vascular cells in the region being treated. Lipid soluble agents are capable or rapidly entering the lipid portion of cell membranes and interacting intracellularly, whereas agents, like deferoxamine, that are not lipid-soluble enter cells much more slowly. Deferoxamine, since it is not lipid soluble, is not useful when administered in a bolus by the intravascular route. However a lipid-soluble iron chelator would be expected to be capable of rapid intravascular administration, because it would be likely to be rapidly taken up by smooth muscle cells in the vessel.

Thus there is a need for an agent which can be delivered other than intravenously and which can rapidly enter vascular smooth muscle cells and prevent their proliferation. Such an agent would be potentially useful in preventing atherosclerosis, restenosis or other adverse outcomes of vascular injury.

SUMMARY

Deferoxamine does not meet these criteria. However, it has been discovered that specific exochelins, described below, are unique iron chelators because they are both lipid-soluble, which enables them to rapidly enter the lipid portion of the cell membrane, and they prevent iron-mediated production of hydroxyl radical or other highly reactive free radicals. As a result, we have demonstrated that they are capable of preventing smooth muscle proliferation. All other iron chelators which are currently available either cannot rapidly enter cells or have not been demonstrated to prevent proliferation of vascular smooth muscle cells.

DRAWINGS

These and other features, aspects and advantages of the present invention will become better understood with reference to the following description, appended claims, and accompanying drawings, where:

FIG. 1 shows the chemical structure of an iron chelate of exochelin (FIG. 1A) (ferriexochelin) and the desferriexochelin (iron free) molecule (FIG. 1B having the side chains specified in FIG. 1C.

FIG. 4b shows the mass spectrometer spectra of the serine containing exochelin of FIG. 4a.

DETAILED DESCRIPTION OF THE INVENTION

Figure 2A:
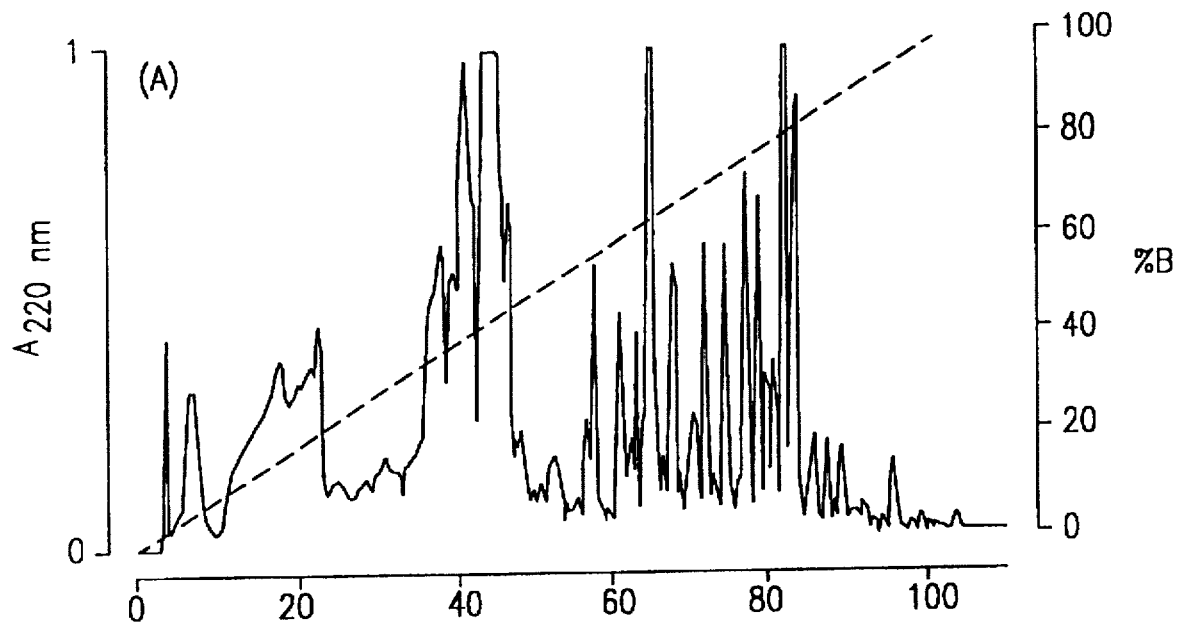
FIG. 2 shows an elution profile of a culture filtrate of *M. tuberculosis* monitored at 220 nm (FIG. 2A) and 450 nm (FIG. 2B).

It has been found that exochelins are lipid soluble agents that can chelate iron and block iron-mediated reactions such as the production of hydroxyl radical through the Fenton reaction. Because of their lipid solubility, exochelins are capable of entering cells much more rapidly than non-lipid soluble iron chelators such as deferoxamine. Lipid solubility may also allow exochelins to localize and chelate iron in different portions of cells than lipid-insoluble iron chelators such as deferoxamine. We have now demonstrated that exochelins are capable of preventing cultured vascular smooth muscle cell proliferation.

It has been also been found that exochelins can block, or significantly reduce, oxidative damage to tissue resulting from the iron-mediated catalysis of tissue/free radical reactions, such as the production of hydroxyl radical ($\bullet$OH) by the Fenton reaction. This reaction is an important cause of reperfusion injury which occurs when blood flow is restored after a temporary interruption. It has been further found that the exochelins are effective to retard or prevent reperfusion injury when administered during reperfusion. Additionally, it has been found that exochelins encompass a much broader class of materials and have a different chemical structure then originally theorized by Macham et al. and Barclay et al.

It has further been found that these materials can chelate a broad range of metals to result in materials not previously known. Besides preventing reperfusion injury, properly modified exochelins can be used to treat certain diseases, and attack certain cells, such as cancer cells. In particular, it is known that the growth of neuroblastoma cells can be negatively affected by the removal of iron using the iron chelating compound deferoxamine without similarly affecting the growth of normal cells. Other applications of exochelins include treatment of iron overload from transfusions or cancer chemotherapy.

As a result of isolating and purifying exochelins, it has been found that exochelins are a family of molecules having a range of molecular weights and various different side chains. Further, purified exochelins have been prepared and their utility as scavengers of free iron, such that they are effective in preventing the formation of tissue damaging hydroxyl radicals ($\bullet$OH), has been demonstrated for the first time. In particular, purified exochelins of *M. tuberculosis* have been isolated and have been shown to effectively remove iron from transferrin, lactoferrin and ferritin at physiological pH without transmitting any of the infectious properties of the bacteria from which they are derived. It has also been demonstrated for the first time that these exochelins block hydroxyl radical formation by the Fenton reaction and, based on the response of cardiac myocytes, can be effective to prevent reperfusion injury after myocardial infarction or vascular insults to other tissue when administered after the attack occurs as well as for several hours after the episode.

While mycobactins have been extensively studied, individual exochelins had not been isolated or purified and their structure and composition had not been previously defined. Further, we have found that prior references have mischaracterized the exochelins, and thus have failed to identify the structure of these compounds. In particular, Macham (ibid.) identified them as a penta- or hexapeptide, having a molecular weight of 750 to 800, containing 3 mol of ε-N-hydroxylysine, εN-acetyl-εN-hydroxylysine, or εN-hydroxyornithine and 1 mol of threonine. We have found that the exochelins have a much broader range of molecular weights, constitute several series of compounds with an identifiable difference in molecular weights, include only 2 mol of ε-N-hydroxylysine and are not peptides. A peptide is a polymer of an amino acid ($NH_2$—CHR—COOH) formed by the condensation of the carboxylic group of a first molecule with the amino group of another molecule to form an amide linkage (—CO—NH—). Exochelins cannot be considered to be peptides. Instead, they contain three amino acids and other structural moieties (salicylic acid, dicarboxylic acids or monoester analogs, and hydroxy carboxylic acids) formed by amide (—NH—CO—), hydroxymate (—NH(OH)—CO—) and ester condensations (—CO—O—). The ferri- and desferri forms are shown in FIG. 1.

Preparation—Exochelins were generated and purified from a virulent (Erdman) and avirulent (H37Ra) strain of *M. tuberculosis*. To enhance the production of *M. tuberculosis* exochelins the bacteria were cultured in an iron deficient medium. In particular, the Erdman strain of *M. tuberculosis* (American type culture collection 35801) and H37Ra (ATCC 25177) were grown on Middlebrook 7H11 agar plates at 37° C. in 5% $CO_2$. After 14 days the bacteria were harvested, suspended in 150 ml of modified Sauton's medium in culture flasks and incubated for 3 to 8 weeks. The modified Sauton's medium contained 0.12 mg/l ferric ammonium citrate without added surfactant.

Iron rich exochelins (ferriexochelins) were then recovered by filtering, saturating with iron and extracting with chloroform and purified by high pressure liquid chromatography (HPLC). Specifically, the supernatant fluid from the above suspension was filtered through successive 0.8 µm and 0.2 µm low-protein binding filters. The exochelins were then loaded with iron by saturating the filtered supernatant fluid by exposure to ferric chloride (150 mg per liter of culture filtrate). The ferric-exochelins were mixed with chloroform (1 volume of culture filtrate per 1.5 volumes of chloroform) and, after separation of the layers, the exochelin rich chloroform layer was removed and stored under anhydrous magnesium sulfate (2 g/l). The chloroform extract was then passed through a fritted glass filter and evaporated by rotary evaporation leaving behind a brown residue.

Figure 2B:
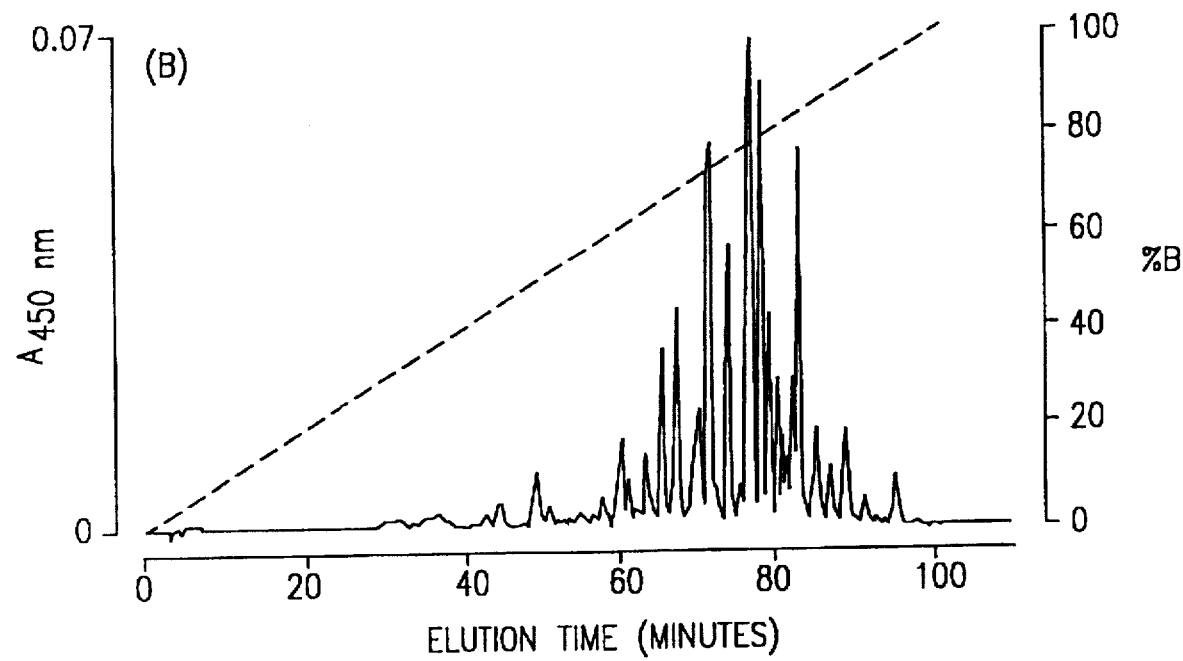

The brown residue was further purified by suspension in 5 ml of a first buffered solution (0.1% trifluoroacetic acid) which was introduced into a liquid chromatography column (C-18 Sep-Pak cartridge). The brown band which formed near the top of the column was eluted with a second buffer (0.1% TFA, 50% acetonitrile). The partially purified material was then diluted three-fold in 0.1% trifluoroacetic acid and subjected to reverse phase high pressure liquid chromatography at a rate of 1 ml/min followed by exposure to a C-18 column. The presence of the iron rich exochelins in the HPLC eluate was detected by simultaneous monitoring of the UV absorbance of the 450 nm peak (iron compounds) and the 220 nm peak which is indicative of amide and aromatic groups. Approximately 5 major and 10 minor peaks, shown in FIG. 2, eluted out of the final C-18 column exhibited a high 450/220 nm absorbance ratio. These were confirmed to be exochelins by mass spectrometry. Major peaks were further purified by a second reverse phase HPLC on an alkyl-phenyl column. The exochelins recovered from the Erdman strain of *M. tuberculosis* were identical to the exochelins recovered from the H37Ra strain.

Characterization—Based on LSIMS and ESI-MS analysis of the numerous peaks, in their ferri-($Fe^{3+}$) form, eluted from the column (see FIG. 3), the iron-exochelins are not confined to the two specific molecules detailed above but include a family of species ranging in mass from 716 to 828 daltons. Each member of the family appears to differ from its neighbor by 14 daltons, reflecting the number of $CH_2$ groups in the $R_1$ alkyl side chain and/or 2 daltons, reflecting the presence of a double bond in the $R_1$ alkyl side chain. Accordingly, the exochelins appear to form two series with the subsequent members of each series differing in mass by 14 daltons, the saturated series having masses of approximately 716, 730, 744, 758, 772, 786, 800, 814 and 828 daltons and the unsaturated series having masses of 742, 756, 770, 784, 798, 812 and 826. Additionally, the presence or absence of a methyl group at $R_3$ (i.e., H or $CH_3$) further defines an additional two series of molecules referred to as the serine ($R_3$=H) and the threonine series ($R_3$=$CH_3$), as confirmed by amino acid analysis. The most polar compounds are to the left of the figure (elute earlier) and the least polar (most soluble in lipid) are to the right. However all the peaks are water soluble. Where more than one peak was found to have the same molecular weight, each peak is further designated A, B or C (i.e., 758A, B and C) to indicate the level of polarity with A representing the most polar compound and the C representing the least polar form. The more polar forms are believed to result from a methyl group attached at a different location in the molecule.

Figure 4A:
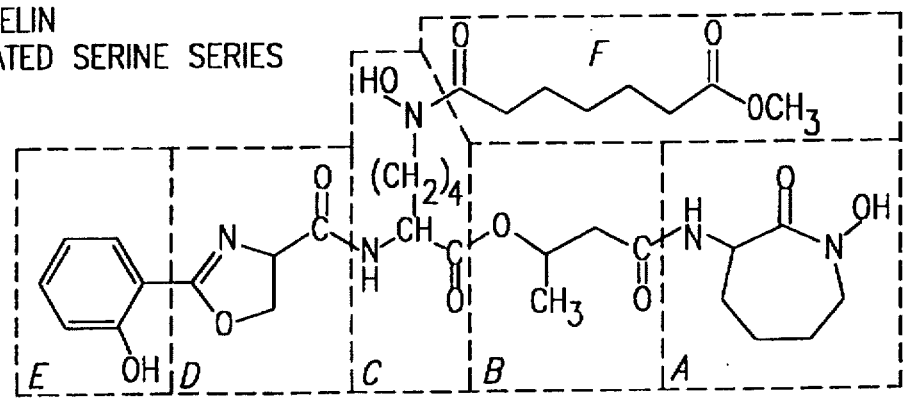
FIG. 4a shows the structure of a major serine-containing exochelin at m/z=720.3.
Figure 4B:
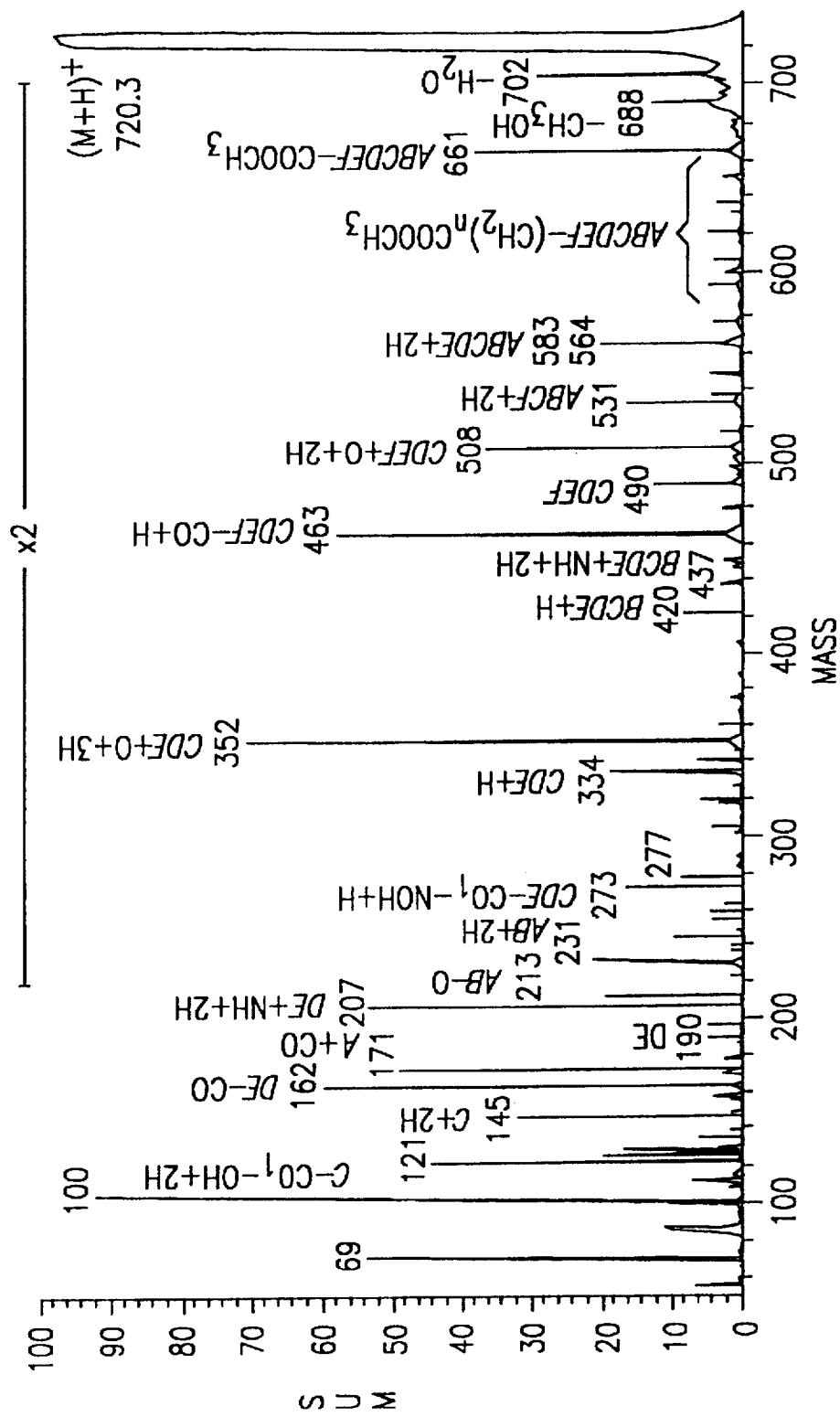

Structure of the Exochelin—FIG. 4 shows the results of tandem mass spectrometric analysis under collision induced dissociation (He floated at 2 keV for a collision energy of 6 keV) of the major saturated serine-containing desferriexochelin with $(M+H)^+$ at m/z 720.3. The fragment ions were assigned to one of the six structural moieties A–F resulting from the cleavage products generated about the amide or ester bonds with the hydrogen transfers relative to the neutral molecule associated with each peak indicated on the spectrum shown in FIG. 4. Acid hydrolysis and methylation of the exochelins resulted in the formation of salicylic acid and pimelic acid. The mass spectrographic analysis indicates that the pimelic acid is present in the exochelin as a methyl ester.

Figure 6A:
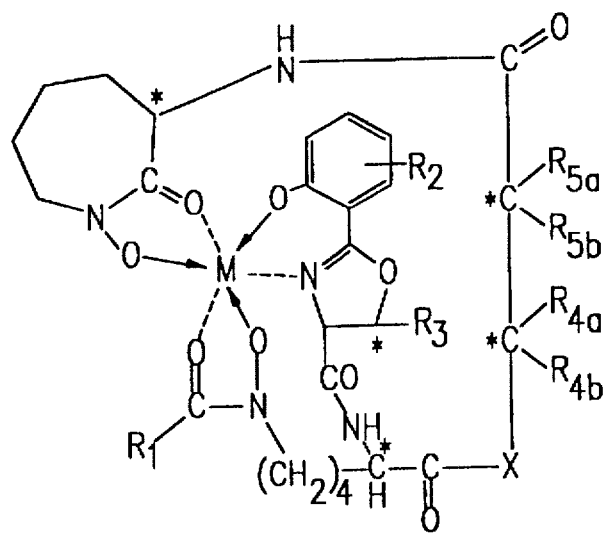
FIG. 6 shows the chemical structure of an iron chelate of exochelin (ferriexochelin) (FIG. 6A) and the desferriexochelin (iron free) molecule (FIG. 6B) with sites for modification identified.
Figure 6B:
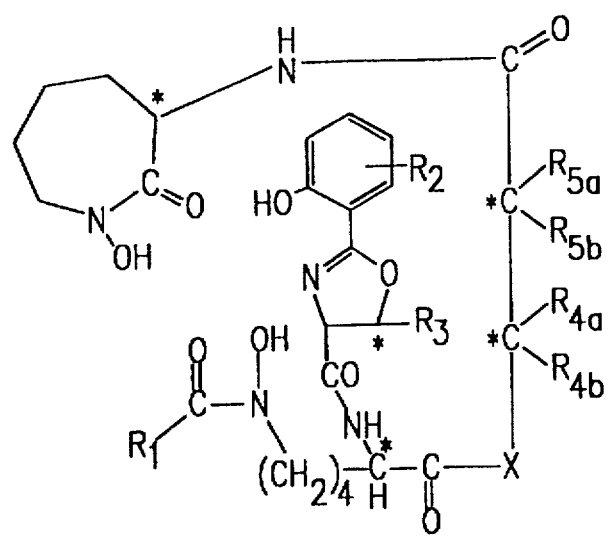

Based on this analysis the general structure of the ferriexochelins and the desferriexochelins is shown in FIG. 1. The methyl group shown in FIG. 1 at the $R_4$ position, as defined in FIG. 6, may be in the $R_5$ position, also defined in FIG. 6. The iron-exochelin core molecule is circular with iron in the center. It contains 3 amino acid moieties (two N-hydroxylysines and 1 serine or threonine, depending on whether $R_3$ is a hydrogen or methyl group). The major difference between exochelins and mycobactins of *M. tuberculosis* is that $R_1$ in the exochelins exists typically as either a saturated alkyl methyl ester (($CH_2$)$_x$$COOCH_3$), a singly unsaturated alkyl methyl ester ($CH_2$)$_x$CH=CH($CH_2$)$_y$COOCH$_3$ or a carboxylic acid and exochelins have a much shorter alkyl side chain than mycobactins with these shorter side chains terminating in methyl ester moieties. These differences provide for the water solubility of the exochelins and their ability to function in the extracellular environment.

Figure 5:
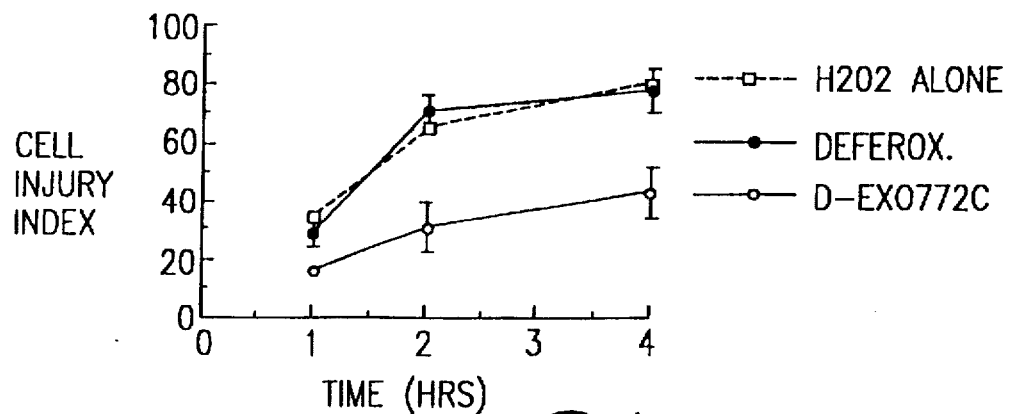
FIG. 5 is a graph comparing the inhibition of cell injury as a result of the use of desferrin-exochelin 772C or deferoxamine on cardiac myocytes.

FIG. 5 compares the cell injury prevention when deferoxamine or a much smaller amount of exochelin are added to a rat cardiac myocyte cell culture treated with $H_2O_2$. This graph demonstrates that exochelin can rapidly enter cells and reduce or prevent damage while deferoxamine has no beneficial result.

Figure 3:
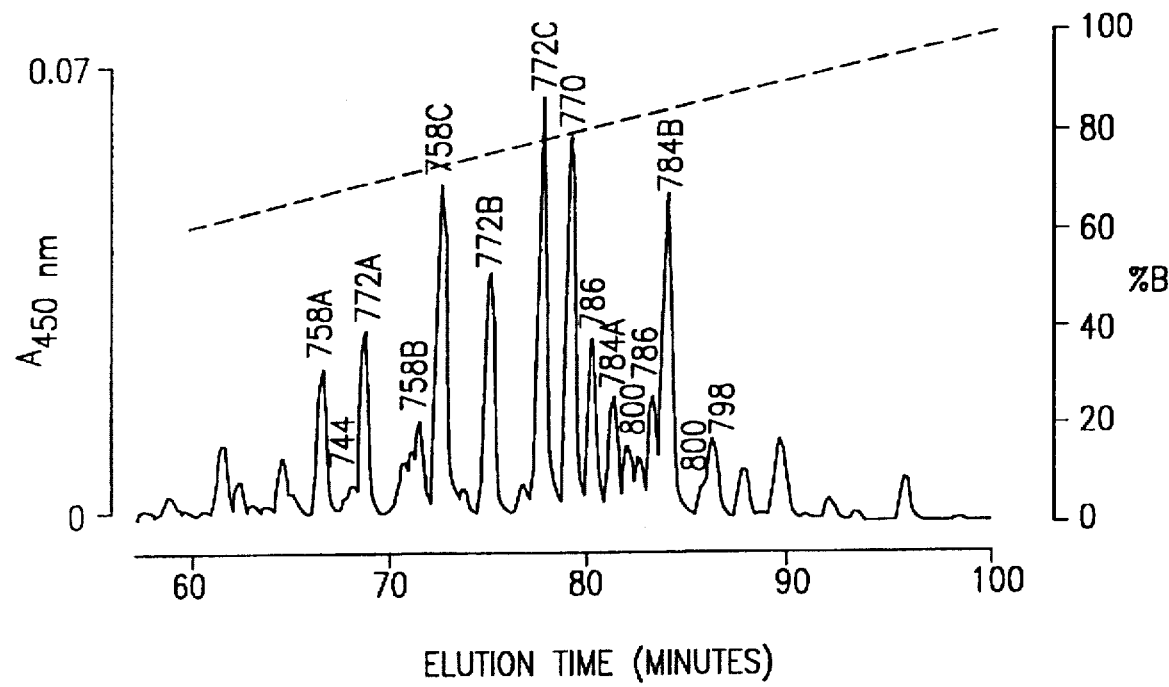
FIG. 3 shows an elution profile of the same filtrate monitored at 450 nm with the molecular weight of each peak shown.

In the examples below the desferri-Exochelins and the ferri-Exochelins are referred to by the mass of the ferri-Exochelins as shown in FIG. 3. A letter following the mass number (A, B, C, etc.) designates that compounds of the same molecular weight but different elution characteristics exist, indicating different location of side chains or different optical orientation which effect the compounds polarity (solubility). Peaks of the same mass are additionally labelled with a letter (A, B, C) by the order in which they elute from the column, with A coming off first, then B, and then C. A number followed by SM designates that the compound is a number of the serine (S) series and a methyl ester (M), while TM designates a member of the threonine (T) series as well as a methyl ester (M).

The mass of the iron free (desferri) form is 53 less than the ferri-form because the ferri-form loses one iron atom (56) but gains 3 H (1) atoms.

EXAMPLE 1

Figure 7:
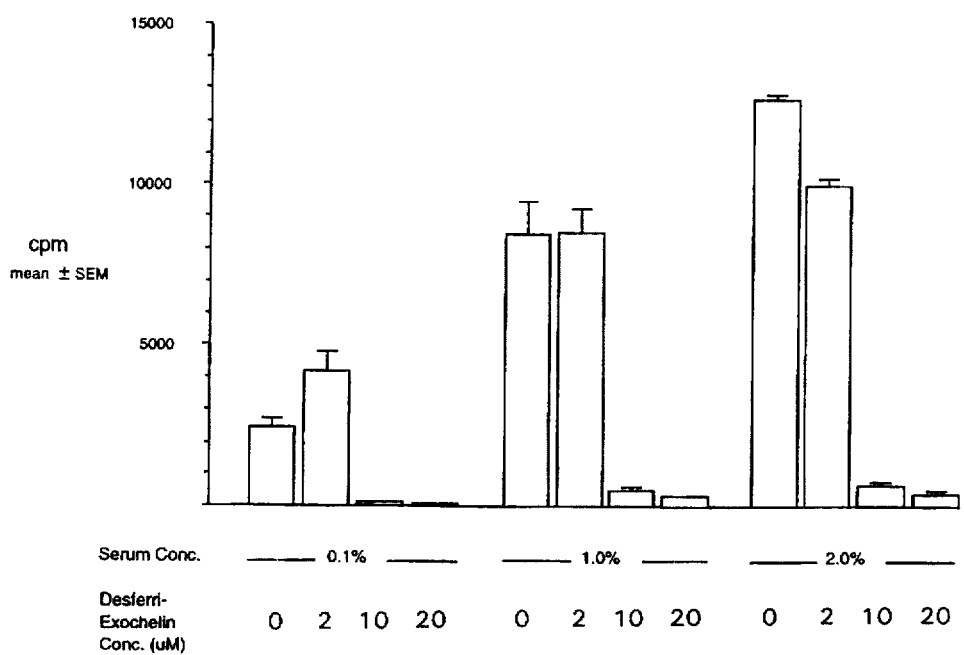
FIG. 7 is a graph comparing several samples of cultured vascular smooth muscle cells treated with different concentrations of desferri-Exochelin.

Human vascular smooth muscle cells were obtained from saphenous vein segments removed in the course of elective surgery. The inner muscular layer of the vein segments was dissected from the remainder of the vessel segment, minced and digested with a mixture of collagenase and elastase at pH 7.4. Four subsequent digestions were then performed sequentially with medium containing bovine trypsin, alpha-chymotrypsin and elastase. This resulted in separation of viable smooth muscle cells from the remaining components of the vessel. After centrifugation to remove debris, the cells were resuspended in 25 cm$^2$ flasks in medium with 10% serum (50% bovine calf serum and 50% serum from newborn human umbilical cord blood, which was heat-inactivated) for two weeks. The cells were then seeded in 24 well culture dishes (20,000 cells/well) for 2 days in 10% serum. The cells were then quiesced in medium with 0.1% bovine serum for three days. The cells were then preincubated for 30 minutes in medium with 0.1% serum. Two, 10, or 20 micromolar concentrations of desferri-Exochelin 772SM (previously designated as 772C, see FIG. 3) were then added to test wells containing either 0.1%, 1%, or 2% bovine serum for 24 hours. Control wells received the same concentrations of serum but did not receive 772SM. Triplicate samples were studied for each condition. Four hours before the end of the 24 hour exposure, 0.5 µCi/ml of tritiated thymidine were added to each well. At the end of the 24 hour incubation period, the cells were lysed and the radioactivity of the contents of each well was measured with a liquid scintillation counter. Results are shown in FIG. 7 which plots the counts for each triplicate group of wells for each of the 12 conditions studied (total=36 wells). The bars represent mean values for each group of three wells and the vertical lines above each bar depict the standard error of the mean. Each group of three well samples is labelled as to the % serum present (0.1%, 1.0% or 2.0%) and the molar concentration of desferri-Exochelin 772SM (0, 2, 10, or 20 µM) if added. At each of the three serum concentrations either 10 or 20 micromolar of desferri-Exochelin 772SM markedly reduced thymidine uptake in comparison with wells containing the same serum concentration but no or low (2 µM) desferri-Exochelin. Since thymidine uptake is a measure of cell proliferation, it can be concluded that desferri-Exochelin 772SM in concentrations greater than 10 micromolar, and particularly in the range of 10–20 micromolar, prevents serum-stimulated human vascular smooth muscle cell growth.

EXAMPLE 2

Figure 8:
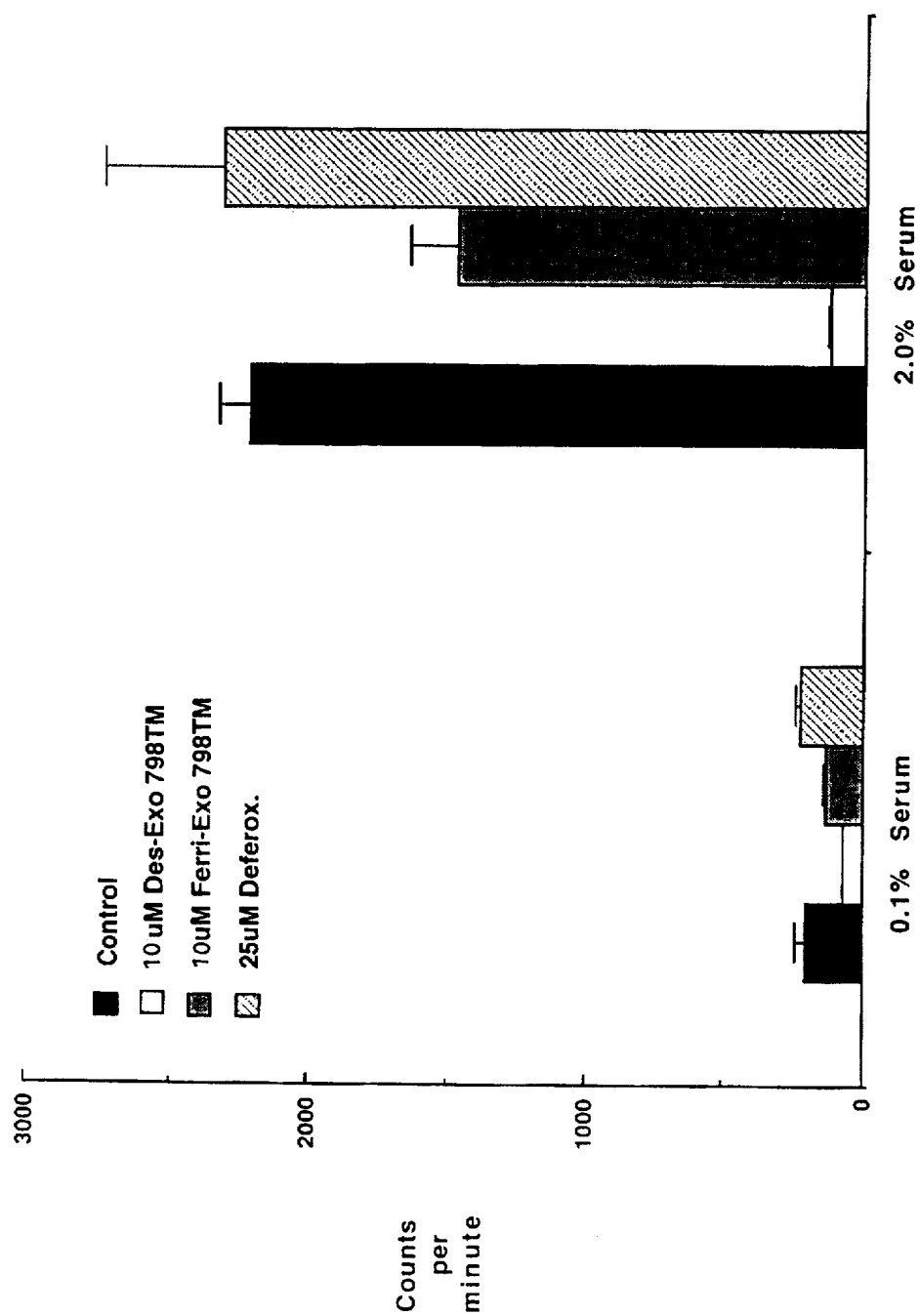
FIG. 8 is a graph comparing the effect of treating vascular smooth muscle cell cultures with desferri-Exochelin, ferri-Exochelin and deferoxamine.

Human vascular smooth muscle cells were obtained and processed in the same manner as described in Example 1. The cells were seeded in 24 well culture dishes (approximately 12,800 cells/well) for 2 days in 10% serum and then quiesced in medium with 0.1% bovine serum for four days. Experiments were then carried out in wells containing either 0.1% or 2% bovine serum for 24 hours. During the 24 hour test period, wells contained no drug (Control), 10 µM desferri-Exochelin 798TM (Des-Exo 798TM), 10 µM ferri-Exochelin 798TM (Ferri-Exo 798TM), or 25 µM deferoxamine (Deferox.). Desferri-Exochelin 798TM (Des-Exo 798TM), and ferri-Exochelin 798TM (Ferri-Exo 798TM) are compounds having masses of 745 and 798 respectively (See FIG. 3). Triplicate samples were studied for each condition. During the last four hours of the 24 hour exposure, 0.5 µCi/ml of tritiated thymidine were added to each well. At the end of the 24 hour incubation period, the cells were lysed and radioactivity measured in the contents of each well with a liquid scintillation counter. Results are shown in FIG. 8 where the counts for each triplicate group of wells for each of the 8 conditions studied are shown (total=24 wells). The bars represent mean values for each group of three wells and the vertical lines above each bar depict the standard error of the mean. Each group of three well samples is labelled as to the % serum present and the molar concentration of drug added, if any. There were only small amounts of thymidine uptake, indicated by counts per minute, in the wells containing 0.1% serum because very little cell proliferation occurs at this serum concentration. However, the control (untreated) wells had high thymidine uptake after 24 hours in 2.0% serum. In contrast, in the wells treated with desferri-Exochelin 798TM, there was virtually no increase in thymidine uptake during exposure to 2.0% serum over levels measured in untreated cells in 0.1% serum. In the wells treated with ferri-Exochelin 798TM, which is fully iron-saturated Exochelin 798TM, and exposed to 2.0% serum there was substantial thymidine uptake but less than was observed in control cells in 2.0% serum. In wells treated with deferoxamine and exposed to 2.0% serum there was similar thymidine uptake to control cells exposed to 2.0% serum. Since thymidine uptake is a measure of cell proliferation, desferri-Exochelin 798TM in a concentration of 10 micromolar prevents serum-stimulated human vascular smooth muscle cell growth. Ferri-Exochelin 798TM has a small inhibiting effect on serum-stimulated human vascular smooth muscle cell growth, and 25 micromolar deferoxamine (2.5 times the concentration of desferri-Exochelin) has no effect on serum-stimulated human vascular smooth muscle cell growth, indicating that the tested exochelin has a cell growth inhibiting effect which is separate from its ability to chelate iron.

EXAMPLE 3

To assess whether lipid-soluble desferri-Exochelins were capable of being rapidly taken up by cardiac tissue during a brief injection, studies were performed in isolated rabbit hearts. The protective effects against reperfusion injury and accumulation of metabolites of hydroxyl radical were measured following a brief injection of desferri-Exochelins into the root of the aorta. Also measured were exochelins in the venous effluent which, in this non-recirculating system, required rapid initial takeup by cardiac tissue of the injected desferri-Exochelins.

Isolated, Perfused Heart Preparation—Fifteen adult New Zealand White rabbits of either sex weighing 2.3–3.5 kg were heparinized (1000 U/kg) and anesthetized with pentobarbital sodium (60 mg/kg i.v.). The hearts were rapidly excised and perfused with modified Krebs-Henseleit buffer using the nonrecirculating Langendorff technique. In order to trap hydroxyl radical isomers, 1 mM salicylic acid was added to the buffer. The buffer perfusate was delivered to the heart through an aortic cannula at a pressure of 73 mm Hg. A fluid-filled latex balloon was inserted into the left ventricle for pressure measurements. Before any pressure measurements, the balloon volume was adjusted to achieve a baseline diastolic pressure of 5 mm Hg and was not readjusted for the remainder of the experiment. Developed pressure was defined as peak systolic pressure minus end diastolic pressure. The first derivative of left ventricular pressure (dP/dt) was obtained with a differentiator circuit. All hearts were paced at 240 beats/min. Coronary effluent was obtained through a needle inserted into the cavity of the left ventricle.

Salicylate Technique for .OH Detection—Salicylate metabolites were quantitated by tandem capillary gas chromatography (GC) and mass spectrometry (MS). Samples and standards were spiked with 2,6-dihydroxybenzoic acid (internal standard) extracted with ethyl acetate (97% efficiency) and derivatized to form the trimethylsilyl ethers with Bis (trimethylsilyl) trifluoroacetamide. The capillary GC separation gave distinct peaks for salicylate, the internal standard (2,6-dihydroxybenzoic acid), and the salicylate metabolites of OH, namely the 2,3- and 2,5-dihydrobenzoic acids. Quantitative analysis was attained using standard curves where the ion ratios of each analyte to internal standard were plotted against concentration.

Authentic standards of 2,3-, 2,4-, 2,5- 3,4- and 2,6-dihydroxybenzoic acid and salicylic acid were purchased. Standard curves were prepared of 2,3-, 2,4-, 2,5- and 3,4-dihydrobenzoic acids in methanol at a series of concentrations ranging from 1 to 1,000 pmol. The internal standard (2,6-dihydroxybenzoic acid) was added at a concentration of 100 pmol. Standards and biological extracts were analyzed in triplicate by GCMS, using a Hewlett Packard 5890 gas chromatograph interfaced to a 5970 mass selective detector. GC conditions consisted of an initial column temperature of 100° C. for 5 minutes which was increased by 10° C. per minute to 300° C. Ions were monitored at m/z 355, 356 and 357 for the dihydrobenzoic acids. All ions had dwell times of 25 ms. Minimal detection levels of the 2,3- and 2,5-dihydrobenzoic acids were in the 200 femtomole concentration range. Measurements in homogenized myocardium were expressed as pmols/g myocardium. Measurements in the coronary effluent were expressed as pmols/g myocardium min.

Figure 9:
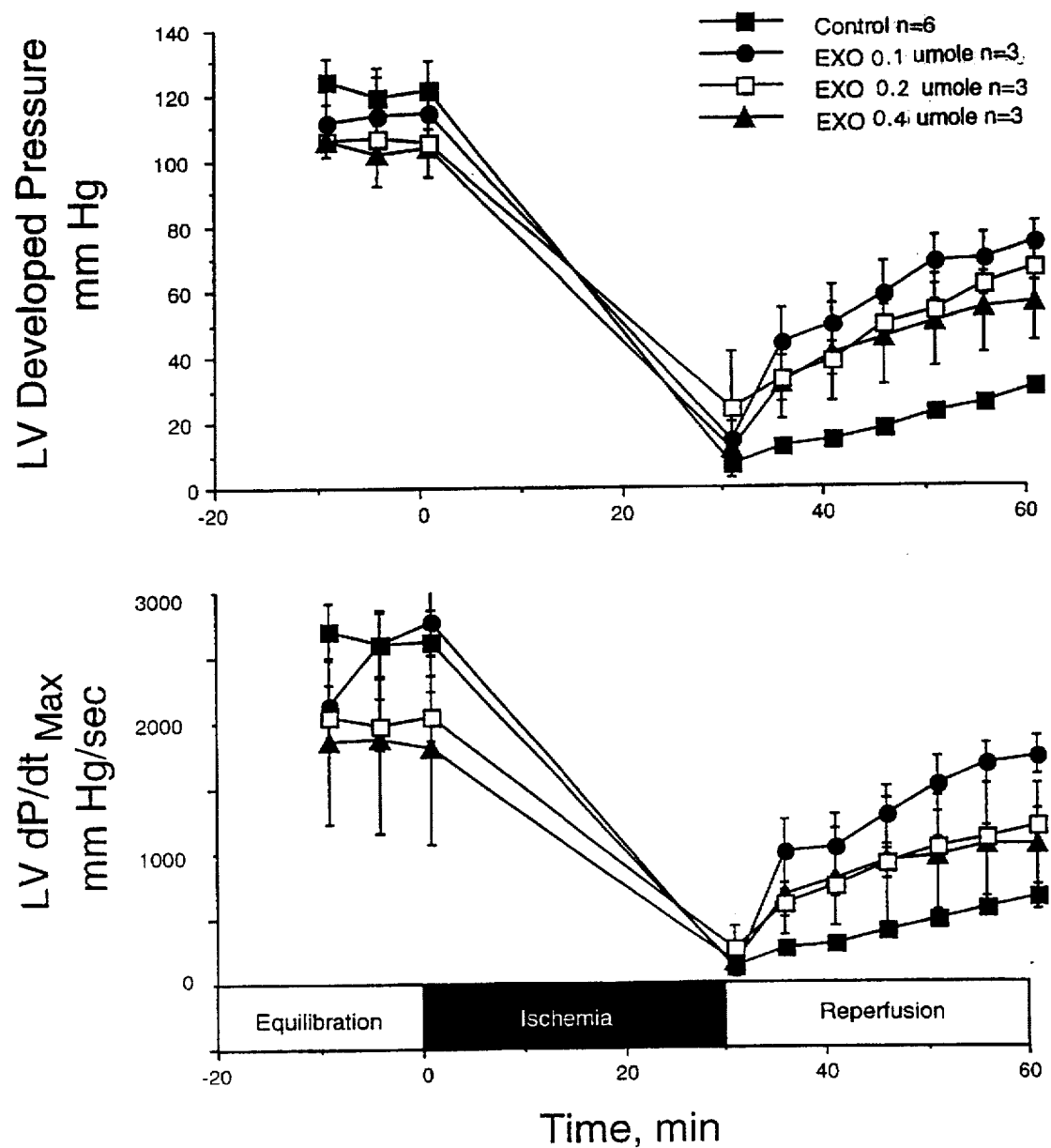
FIG. 9 is a graph showing the effects on left ventricular (LV) systolic function during recovery from ischemia at different dosages of desferri-Exochelin.

Protocol—After a 10-min equilibrium period during which baseline data was acquired, the aortic cannula was clamped and the pacemaker turned off. After a 30-min ischemic period, reperfusion was initiated and pacing was resumed. During the 30-min reperfusion period, pressures were recorded and coronary effluent was collected every 5 mins. At the end of the reperfusion period, the hearts were immediately freeze-clamped with aluminum tongs cooled in liquid nitrogen and stored at −70° C. for subsequent analysis. The controls received normal saline and the treated hearts received an infusion of desferri-Exochelin in normal saline at a dose of one of 0.1, 0.2, or 0.4 μmoles into the aortic root during the first 3 minutes of reperfusion Results—Six control (untreated) hearts, three hearts treated with 0.1 μmole of desferri-Exochelins, three hearts treated with 0.2 μmole of desferri-Exochelins, and three hearts treated with 0.4 μmole of desferri-Exochelins were studied. Effects on left ventricular (LV) systolic function during recovery from ischemia are shown in FIG. 9. The control hearts showed only minimal improvement in left ventrical pressure as represented by its first positive derivative (LV dp/dt MAX) and developed pressure during the 30 minute recovery period as indicated by the entire pressure curve over the 30 minute period. By the end of the 30 minute recovery period both LV dp/dt MAX and LV developed pressure increased more than two-fold at all doses of desferri-Exochelin compared with the control. There was a direct relationship of dosage to response with the highest tested concentration showing at least a three-fold increase. Therefore, it has been shown that hearts treated with 0.1, 0.2, and 0.4 μmoles of desferri-Exochelin administered into the aortic root over a three minute period demonstrated substantial improvement in LV systolic function compared with controls, and there is a direct dose response relationship.

Figure 10:
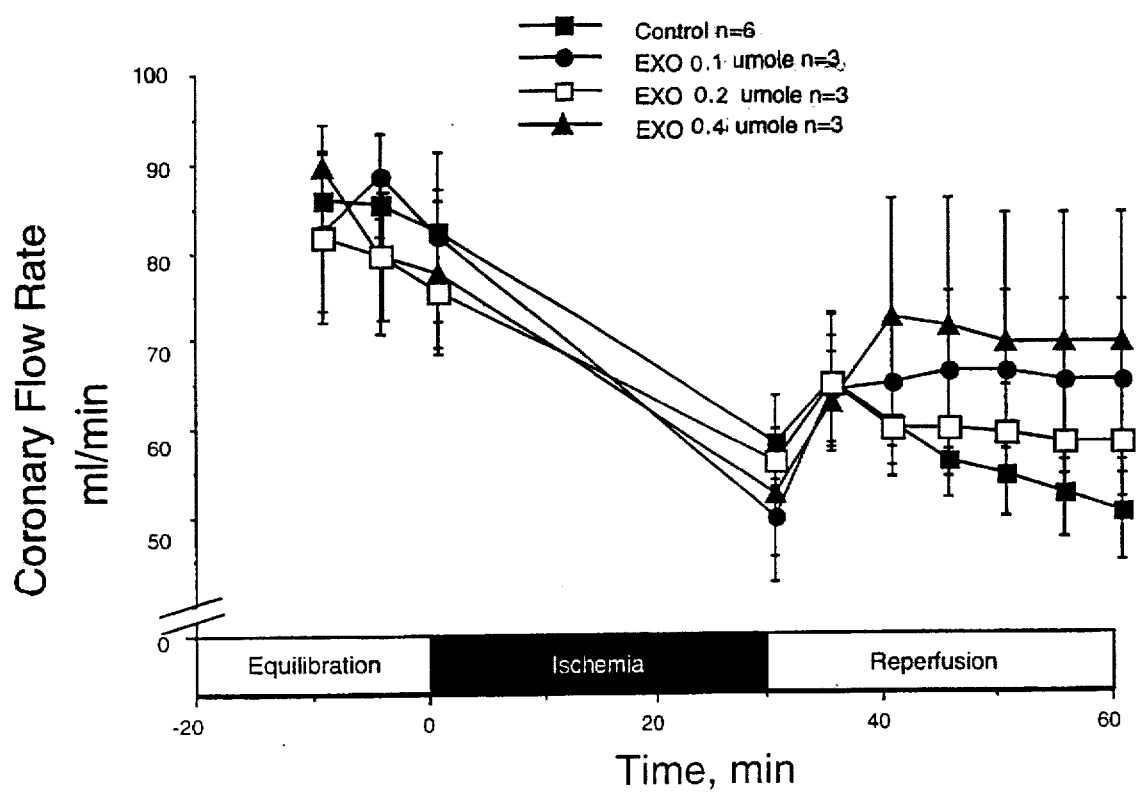
FIG. 10 is a graph showing measurements of coronary effluent flow before and after ischemia at different dosages of desferri-Exochelin.

FIG. 10 shows measurements of coronary effluent flow before and after ischemia. Coronary flow during reperfusion was lower in the control hearts then in the desferri-Exochelin hearts. The higher coronary flows in the treated hearts during reperfusion reflect a reduction in coronary vascular injury.

Figure 11:
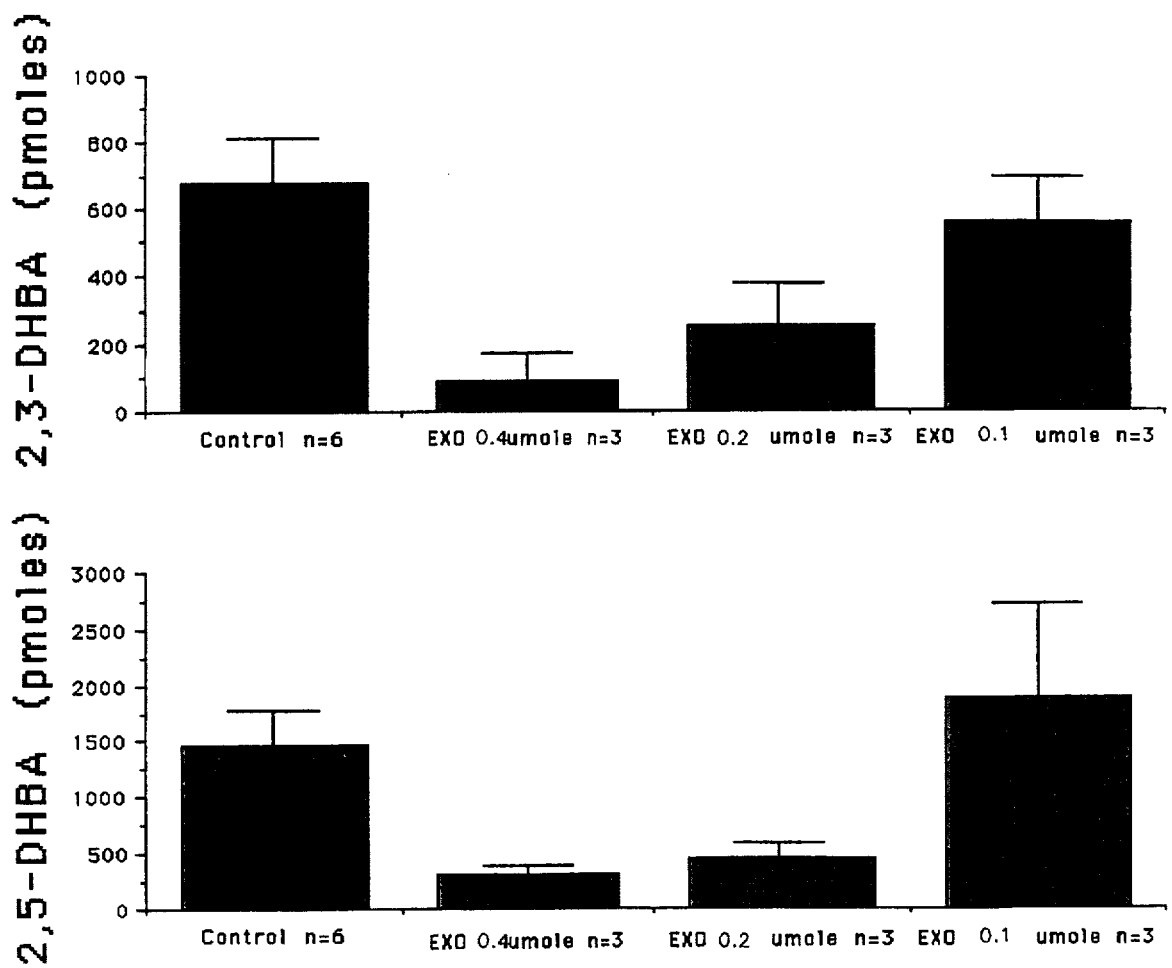
FIG. 11 is a graph showing measurements of 2,3 DHBA and 2,5 DHBA, in cardiac tissue after 30 minutes of reperfusion at different dosages of desferri-Exochelin.

FIG. 11 shows measurements of 2,3 DHBA and 2,5 DHBA in cardiac tissue after 30 minutes of reperfusion. 2,3 DHBA and 2,5 DHBA are salycylate isomers of the hydroxyl radical. Six untreated hearts and 3 hearts at each concentration of desferri-Exochelin (0.1, 0.2, and 0.4 μmole) were studied. Both the 2,3- and 2,5-DHBA levels were reduced in the treated hearts in a dose-related manner indicating that there is a dose-related reduction in hydroxyl radical metabolites in the hearts treated with desferri-Exochelins. This is due to reduced production of hydroxyl radical as a result of iron chelation by the desferri-Exochelins.

In one of the hearts infused with 0.2 μmoles of lipid-soluble desferri-Exochelins, the venous effluent was collected every five minutes during reperfusion and the amount of exochelin present was measured. This heart was infused with relatively nonpolar (highly lipid-soluble) substantially iron free exochelins—0.042 μmoles of 770SM (alternatively designated as 770 in FIG. 3), 0.110 μmoles 784SM (alternatively designated as 784B in FIG. 3) and 0.047 μmoles 798TM (alternatively designated as 798 in FIG. 3). The exochelins infused into the root of the aorta were <5% iron saturated (>95% in the desferri-form). During reperfusion, the amounts of desferri-Exochelins and the total amount of exochelins (both desferri- and ferri-forms) in the effluent were quantified. The amount of ferri-Exochelin in the effluent was assayed by extracting a sample of the effluent with chloroform to remove the exochelins, evaporating this chloroform extract to dryness, suspending the exochelins in buffer, subjecting the extract to reverse-phase high pressure liquid chromatography, measuring the area under the 450 nm absorbance peak corresponding to each exochelin, and converting this area to mass units using a standard curve. The total amount of exochelin in the effluent was determined by saturating an aliquot of the effluent with iron to convert all exochelins in the sample to the ferri-Exochelin form, and then assaying the exochelins by the same procedure just described. The effluent collected during the first five minutes of reperfusion contained 0.048 μmoles of exochelin. There was no measurable exochelin in the later samples. Since there was a total of 0.2 μmoles of Exochelin infused into the aorta, the percentage recovered in the effluent was 0.048 μmoles/0.2 μmoles×100=23.8%. This indicated that substantial amounts (76.2%) of the injected exochelins were retained in the heart. Further, the exochelins measured in the effluent were 25.9% iron saturated. Hence, even during a single passage through the heart, desferri-Exochelins were able to acquire substantial quantities of iron.

The combined effect of the desferri-Exochelins on left ventricular systolic function and production of hydroxyl radical metabolites, the reduced quantity of exochelins in the coronary effluent, and the evidence that a substantial quantity of the desferri-Exochelins infused into the heart acquired iron during their passage through the heart confirm that physiologically effective quantities of desferri-exochelins are taken up by the heart during a single, brief injection near the origin of the coronary arteries.

As has been demonstrated in Example 1 (FIG. 7) above, the desferri-Exochelins are capable of preventing proliferation of vascular smooth muscle. This finding in combination with the results of the other examples shows that these compounds are useful in preventing diseases related to vascular smooth muscle cell proliferation such as atherosclerosis, vascular restenosis following coronary angioplasty or coronary bypass surgery or other forms of vascular injury or disease including systemic hypertension and various forms of pulmonary hypertension. As has been demonstrated in Example 8 above, the desferri-form of an Exochelin prevents proliferation of vascular smooth muscle, whereas the ferri-form of this Exochelin only modestly inhibits, and 2.5 times as much of a non-lipid soluble iron chelator, deferoxamine, has no effect on human vascular smooth muscle proliferation. As has been demonstrated in Example 9 above, the desferri-Exochelins are capable of entering the heart sufficiently rapidly to chelate iron and prevent adverse oxidant effects when given as a single brief injection. This unique property of desferri-Exochelins indicates that a single dose of exochelin, when delivered into a treated vessel following or during angioplasty or vascular surgery, prevents vascular injury. Deferoxamine, the only other iron chelator suggested to have potential for preventing vascular smooth muscle cell proliferation, requires continuous intravenous administration because it is not rapidly taken up by cells. Even when delivered continuously, there is considerable doubt whether high enough non-toxic doses of this polar, lipid-insoluble iron chelator (deferoxamine) can be achieved with intravenous administration to protect vessels against injury. In contrast, local administration of desferri-Exochelins into the injured or diseased vessel achieves rapid and effective physiological responses. In addition, the demonstration of modest inhibition of proliferation of vascular smooth muscle by the ferri-form of an Exochelin is evidence of a benefit of Exochelins that is separate from its iron chelating property.

While the structure of exochelins recovered from *M. tuberculosis* is shown in FIG. 1, it is known that other mycobacteria can generate exochelins and that these exochelins may have different structure and include different amino acids depending on the mycobacteria from which they are derived. However, all exochelins will behave in a similar manner and exist in similar series with subsequent members thereof having a similar progression of molecular weights. The effectiveness of the different members of the series will also depend on the relative polarity of the molecules. Therefore, the invention contemplates exochelins generated from other mycobacteria including, but not limited to, *M. tuberculosis, M. microti, M. bovis, M. africanum, M. kansasii, M. marinum, M. gastri, M. nonchromogenicum, M. terrae, M. triviale, M. malmoense, M. shimoidei, M. gordonae, M. asiaticum, M. szulgai, M. simiae, M. scrofulaceum, M. avium, M. intracellulare, M. xenopi, M. ulcerans, M. haemophilum, M. farcinogenes, M. lepraemurium, M. paratuberculosis, M. chelonae* subsp. *chelonae, M. chelonae* subsp. *abscessus, M. fortuitum, M. chitae, M. senegalense, M. agri, M. smegmatis, M. phlei, M. thermoresistibile, M. aichiense, M. aurum, M. chubuense, M. duvalii, M. flavescens, M. gadium, M. givum, M. komossense, M. neoaurum, M. obuense, M. parafortuitum, M. rhodesiae, M. sphagni, M. tokaiense* or *M. vaccae*.

It is also contemplated that exochelins can be modified to effect their solubility properties, metal chelating ability or cellular absorption rates. In particular, referring to the structures of the metal containing and metal free compounds shown in FIG. 6A and 6B, the following substitutions are contemplated:

$R_1$=$(CH_2)_nCH_3$ as a linear or branched chain; $(CH_2)_nCOOH$, a fatty acid; $(CH_2)_nCOOR$, a fatty acid ester where R is an alkyl group; $(CH_2)_nCONH_2$;

$R_2$=a substitution at any of the 4 open ring sites of alkyl groups, sulfonamides, hydroxyl, halogen, acetyl, carbamyl, amines, $NO_2$ or any combination thereof;

$R_3$—the H (serine) or $CH_3$ (threonine) can be replaced by side chains found on β-hydroxy amino acids which are capable of forming cyclic oxazoline structures.

$R_{4a}$ and $R_{4b}$=H, $CH_3$ or other alkyl or substituted alkyl groups;

$R_{5a}$ and $R_{5b}$=H, $CH_3$ or other alkyl or substituted alkyl groups; X=O, NH, S, $CH_2$;

M=mono-, di-, or trivalent metals such as Pb, Al, Cd, Ni, Ag, Au, As, Mg, Mn, Zn, Cu, Ru, Nb, Zr, Ta, V, Ga, Pt, Cr, Sc, Y, Co, Ti, Na, K;

*represents chiral centers which may be R or S;

The various hydroxyl groups (OH) involved in chelating the metal can be replaced by various functional groups, such as H or a halogen, to vary the affinity of the compound for the chelated metal or to convert the molecule into a metal antagonist.

Based on these results it is concluded that the delivery of an effective amount of a desferri-Exochelin to a living organism such as an animal or a human being by oral, intravenous or direct delivery to the site at which the effect is desired will a) protect blood vessels in a living organism from restenosis due to proliferation of vascular smooth muscle cells following angioplasty or vascular surgery, b) prevent or slow the progression of atherosclerosis within the patient, c) prevent or slow the progression of systemic hypertension of the patient, d) prevent or slow the progression of radiation damage to the vasculature, e) prevent or slow the progression of stenosis or closure of bypass grafts to the coronary arteries or other blood vessels following a surgical procedure, f) prevent or slow the progression of various forms of pulmonary hypertension, including but not limited to hypoxic, neonatal, and primary pulmonary hypertension, and g) prevent or slow the progression of angiogenesis (new vessel formation). These conclusions are reached because each of these enumerated events are the result of the uncontrolled and undesired growth and/or proliferation of trauma or disease induced tissue growth, all of which will be controlled by the delivery of desferri-Exochelins.

All the diseases referred to above involve vascular smooth muscle proliferation as a critical mechanism. For example restenosis following dilation or other procedures to remove obstructions in arteries, such as angioplasty or atherectomy, involves proliferation of the vascular smooth muscle at the site where the procedure was performed, resulting in the vessel again becoming obstructed. This process is initiated within the first few hours after angioplasty or atherectomy. The examples above indicate that intracoronary injection of a bolus of desferri-Exochelin immediately after an angioplasty or atherectomy procedure will inhibit vascular smooth muscle proliferation during this critical period when the restenosis process would usually begin, and thereby prevent restenosis from occurring. Since restenosis occurs in a high percentage of angioplasty procedures, and intracoronary injection is easy to accomplish immediately after angioplasty or atherectomy, both of which require the use of intracoronary catheters, the delivery of desferri-Exochelins offers a new form of treatment for this very common and serious problem. No other agent is known which can be injected as an intravascular bolus, which is rapidly taken up by cardiovascular tissue, and which also prevents vascular smooth muscle growth. Since intracoronary catheters can be left in place only for brief periods, rapid uptake of any agent used for treatment is essential.

Use of desferri-Exochelins is a novel treatment for restenosis. The lipid solubility of the desferri-Exochelins makes them uniquely capable of rapid takeup by tissue, a property not shared by non-lipid soluble agents such as the iron chelator deferoxamine, and also makes them uniquely attractive for preventing oxidation of low density lipoprotein cholesterol. Two essential mechanisms for the formation of the atherosclerotic plaques, which form the vascular obstructions in coronary artery disease and other vascular conditions, are take up of oxidized low density lipoprotein cholesterol in the vessel wall and vascular smooth muscle proliferation. Since desferri-Exochelins are lipid-soluble antioxidants they are capable of preventing oxidation of low density lipoprotein cholesterol as well as preventing smooth muscle proliferation. No other agent, and particularly non-lipid soluble iron chelators such as deferoxamine, has such a combination of properties. Therefore, desferri-Exochelins are a novel treatment for prevention of atherosclerosis. Chronic administration of desferri-Exochelins by oral or transcutaneous routes is proposed as a potential treatment to prevent formation of atherosclerotic plaque. Similarly chronic administration by oral, transcutaneous or inhaled routes could prevent the smooth muscle proliferation that is an integral mechanism of systemic or pulmonary hypertension or irradiation-induced vascular injury. No other agent is suitable for chronic administration by such routes and yet is capable of preventing the vascular smooth muscle proliferation essential to these processes. For example deferoxamine, a non-lipid soluble iron chelator must be given intravenously by prolonged infusions and is not suitable or effective. Further there has been no evidence of toxicity of desferri-Exochelins at effective anti-proliferative or antioxidant concentrations of these agents in vascular smooth muscle, myocardial, or vascular endothelial cells.

Although the present invention has been described in considerable detail with reference to certain preferred versions and uses thereof, other versions and uses are possible. For example, variations of the described exochelins including optical isomers and modified compounds as described above can have similar or improved beneficial properties. Further, it is contemplated that exochelins generated by other bacteria would also be useful for the described procedures. *M. bovis* BCG has the same exochelins as *M. tuberculosis*. *M. avium* has very similar exochelins. However, the utility disclosed herein is not limited to these listed exochelins. Further, it is believed that the utility of exochelins includes the slowing of the formation and growth of new blood vessels in the body and organs such as the eye. Therefore, the spirit and scope of the appended claims should not be limited to the description of the preferred versions contained herein.

What is claimed is:

1. A method of protecting blood vessels in a living organism from restenosis due to proliferation of vascular smooth muscle cells following angioplasty or vascular surgery, by inhibiting said vascular smooth muscle proliferation, comprising the administration to a living organism in need of such treatment of a composition containing an effective amount of a desferri-Exochelin.

2. The method of claim 1 wherein the administration of the composition containing an effective amount of a desferri-Exochelin is by direct intraarterial delivery.

3. The method of claim 1 wherein the administration of the composition containing an effective amount of a desferri-Exochelin is by systemic intravenous delivery.

4. A method of preventing or slowing the progression of atherosclerosis in a living organism by inhibiting vascular smooth muscle proliferation associated therewith comprising the administration of a composition containing an effective amount of a desferri-Exochelin to a living organism in need of such treatment.

5. The method of claim 4 wherein the effective amount of a desferri-Exochelin is delivered orally.

6. The method of claim 4 wherein the effective amount of a desferri-Exochelin is delivered intravenously.

7. A method of preventing or slowing the progression of systemic hypertension in a living organism by inhibiting vascular smooth muscle proliferation associated therewith comprising administration of a composition containing an effective amount of a desferri-Exochelin to a living organism in need of such treatment.

8. The method of claim 7 wherein the effective amount of a desferri-Exochelin is delivered orally.

9. The method of claim 7 wherein the effective amount of a desferri-Exochelin is delivered intravenously.

10. A method of preventing or slowing the progression of radiation damage to the vasculature of a living organism by inhibiting vascular smooth muscle proliferation associated therewith comprising administration of a composition containing an effective amount of a desferri-Exochelin to a living organism in need of such treatment.

11. The method of claim 10 wherein the effective amount of a desferri-Exochelin is delivered orally.

12. The method of claim 10 wherein the effective amount of a desferri-Exochelin is delivered intravenously.

13. A method of preventing or slowing the progression of stenosis or closure of bypass grafts to the coronary arteries or other blood vessels following a surgical procedure in a living organism by inhibiting vascular smooth muscle proliferation associated therewith comprising administration to a living organism in need of such treatment of a composition which contains an effective amount of a desferri-Exochelin.

14. The method of claim 13 wherein the effective amount of a desferri-Exochelin is delivered orally.

15. The method of claim 13 wherein the effective amount of a desferri-Exochelin is delivered intravenously.

16. A method of preventing or slowing the progression of pulmonary hypertension in a living organism by inhibiting vascular smooth muscle proliferation associated therewith comprising the administration to a living organism in need of such treatment of a composition which contains an effective amount of a desferri-Exochelin.

17. The method of claim 16 wherein the effective amount of a desferri-Exochelin is delivered orally.

18. The method of claim 16 wherein the effective amount of a desferri-Exochelin is delivered intravenously.

19. The method of claim 16 wherein the effective amount of a desferri-Exochelin is inhaled by the organism.

20. A method of preventing or slowing the progression of hypoxic, neonatal, and primary pulmonary hypertension in a living organism by inhibiting vascular smooth muscle proliferation associated therewith comprising the administration to a living organism in need of such treatment of a composition which contains an effective amount of a desferri-Exochelin.

21. A method of inhibiting vascular smooth muscle cell proliferation in a living organism in need of such treatment comprising the administration to said living organism of a composition which contains an effective amount of a desferri-Exochelin derived from *Mycobacterium tuberculosis*.

22. A method of inhibiting the new vessel formation in a living organism in need of such treatment comprising the administration to said living organism of a composition which contains an effective amount of a desferri-Exochelin.

23. The method of claim 22 wherein the desferri-Exochelin is delivered orally of intravenously.

24. The method of claim 22 wherein the desferri-Exochelin is delivered intraocularly and prevents the formation of new blood vessels in the eye.

* * * * *